United States Patent [19]
Daftary

[11] Patent Number: 5,759,034
[45] Date of Patent: Jun. 2, 1998

[54] ANATOMICAL RESTORATION DENTAL IMPLANT SYSTEM FOR POSTERIOR AND ANTERIOR TEETH

[76] Inventor: Fereidoun Daftary, 9001 Wilshire Blvd., No. 205, Beverly Hills, Calif. 90211

[21] Appl. No.: 758,400

[22] Filed: Nov. 29, 1996

[51] Int. Cl.⁶ .................................................. A61C 8/00
[52] U.S. Cl. ........................................ 433/173; 433/172
[58] Field of Search ................................. 433/172, 173, 433/174, 175

[56] References Cited

U.S. PATENT DOCUMENTS

| | | | |
|---|---|---|---|
| 2,857,670 | 10/1958 | Kiernan, Jr. | 433/175 |
| 4,904,187 | 2/1990 | Zingheim | 433/173 |
| 5,015,186 | 5/1991 | Detsch | 433/173 |
| 5,030,095 | 7/1991 | Niznick | 433/173 |
| 5,035,619 | 7/1991 | Daftary | 433/173 |
| 5,049,074 | 9/1991 | Otani et al. | 433/173 |
| 5,052,931 | 10/1991 | Kirsch | 433/173 |
| 5,073,111 | 12/1991 | Daftary | 433/173 |
| 5,145,371 | 9/1992 | Jorneus | 433/173 |
| 5,145,372 | 9/1992 | Daftary | 433/173 |
| 5,297,963 | 3/1994 | Daftary | 433/172 |
| 5,316,476 | 5/1994 | Krauser | 433/173 |
| 5,368,483 | 11/1994 | Sutter et al. | 433/173 |
| 5,431,567 | 7/1995 | Daftary | 433/172 |
| 5,489,210 | 2/1996 | Hanosh | 433/173 |

*Primary Examiner*—John J. Wilson
*Attorney, Agent, or Firm*—Thomas I. Rozsa; Tony D. Chen

[57] ABSTRACT

An anatomical restoration dental implant system for posterior and anterior teeth comprising an anatomic implant fixture which is press-fitted within the tapered alveolus of a patient's jawbone, a matching abutment member seated above the anatomic implant fixture and a bolt member for securing the abutment member to the anatomic implant fixture. The implant fixture has a head section with a bevel periphery top surface and a tapered shaft section with a bottom end. The matching abutment member has a bottom end which has a complementary interior bevel periphery surface, where the abutment member is installed over the top end of the implant fixture such that the complementary interior bevel periphery surface of the abutment member matches the bevel periphery surface of the top end of the implant fixture, thereby providing a perfect match therebetween.

61 Claims, 10 Drawing Sheets

ANATOMICAL RESTORATION DENTAL IMPLANT SYSTEM FOR POSTERIOR AND ANTERIOR TEETH

BACKGROUND OF THE INVENTION

1. Field of the Invention

The present invention generally relates to the field of anatomical dental implants with matching abutment members. In particular, the present invention relates to a system providing a tooth analogue which results in a restoration having tissue-implant profiles similar to that of a natural tooth and its surrounding gingiva. The present invention also relates to fitting a tooth with a temporary crown and final prosthesis after the implant structure has been inserted into the jawbone and the surrounding tissue has healed.

2. Description of the Prior Art

The inventor and applicant of the present invention has been practicing anatomical restoration dental implant surgeries for many years and is the patentee of a series of United States Patents related to anatomical restoration dental implant systems which are listed below. While the patentee's prior art anatomical restoration dental implant systems function adequately, the patentee has continuously sought to further improve his products for the dentistry industry. The following is a list of the applicant's patents:

1. U.S. Pat. No. 5,035,619 issued to Daftary on Jul. 30, 1991 for "Anatomical Restoration Dental Implant System With Improved Healing Cap And Abutment" (hereafter "the '619 Daftary Patent");

2. U.S. Pat. No. 5,073,111 issued to Daftary on Dec. 17, 1991 for "Anatomical Restoration Dental Implant System" (hereafter "the '111 Daftary Patent");

3. U.S. Pat. No. 5,145,372 issued to Daftary on Sep. 8, 1992 for "Anatomical Restoration Dental Implant System With Reinforced Healing Cap And Abutment" (hereafter "the '372 Daftary Patent");

4. U.S. Pat. No. 5,297,963 issued to Daftary on Mar. 29, 1994 for "Anatomical Restoration Dental Implant System With Interlockable Elliptical Healing Cap Assembly And Matching Abutment Member" (hereafter "the '963 Daftary Patent"); and 5. U.S. Pat. No. 5,431,567 issued to Daftary on Jul. 11, 1995 for "Anatomical Restoration Dental Implant System With Interlockable Various Shaped Healing Cap Assembly And Matching Abutment Member" (hereafter "the '567 Daftary Patent").

The '619 Daftary Patent discloses an assembly of a two-piece healing cap and a matching abutment for improving the healing process of the gingival tissue.

The '111 Daftary Patent discloses an anatomical restoration dental implant system for implanting a tooth analogue in the alveolus of the jawbone. The system comprises an implantable fixture implanted through an opened gingival tissue into the alveolus of the jawbone. A cover screw is used for sealing the hollow of the implant fixture during the time the jawbone is growing about the implant fixture. After osseointegration of the implant fixture, the gingiva is reopened and the cover screw is removed and replaced by a healing cap.

The '372 Daftary Patent discloses a reinforced assembly of a two-piece healing cap and a matching abutment. The two-piece healing cap configurations are designed to prevent the unnecessary damage or delay to the healing of the gingival tissues.

The '963 Daftary Patent discloses an anatomical restoration dental implant system with an interlockable elliptical healing cap assembly and a matching abutment member for supporting a tooth analogue with an elliptical root. The healing cap assembly comprises an integral bolt member which has a widened head segment and an elongated shaft segment. The healing cap assembly also comprises a healing cap member which has a divergent body with a larger elliptical end. The healing cap member and the bolt member are interlockable by threading the proximal section of the shaft segment of the bolt member into the distal section of the interior bore of the healing cap member.

The '567 Daftary Patent discloses an anatomical restoration dental implant system with an interlockable various shaped healing cap assembly and a matching abutment member for supporting a tooth analogue with a rounded triangle shaped root. The healing cap assembly comprises an integral bolt member and a healing cap member, which are interlockable. The matching abutment has a bolt segment which is identical to the bolt member of the healing cap assembly, and a frusto-conical shaped head segment. The large end of the frusto-conical shaped head segment of the abutment member is circular shaped and smaller than the rounded triangle shaped end of the healing cap member, such that when the abutment member is attached to the healing cap member, a rounded triangle shaped shoulder is created for matching perfectly with the rounded triangle shaped root of the tooth analogue.

In addition, the following nine (9) prior art patents were uncovered in the pertinent field of the present invention:

1. U.S. Pat. No. 5,015,186 issued to Detsch on May 14, 1991 for "Dental Implant Attachment System" (hereafter "the Detsch Patent");

2. U.S. Pat. No. 5,030,095 issued to Niznick on Jul. 9, 1991 for "Angled Abutment For Endosseous" (hereafter "the Niznick Patent");

3. U.S. Pat. No. 5,049,074 issued to Otani et al. on Sep. 17, 1991 for "Dental Implant" (hereafter "the Otani Patent");

4. U.S. Pat. No. 5,052,931 issued to Kirsch on Oct. 1, 1991 for "Enossal Implant" (hereafter "the Kirsch Patent");

5. U.S. Pat. No. 5,145,371 issued to Jorneus on Sep. 8, 1992 for "Distance Member" (hereafter "the Jorneus Patent");

6. U.S. Pat. No. 5,368,483 issued to Sutter et al. on Nov. 29, 1994 for "Device-For Fixing A Dental Prosthesis To A Jaw Bone" (hereafter "the Sutter Patent");

7. U.S. Pat. No. 5,458,488 issued to Chalifoux on Oct. 17, 1995 for "Dental Implant And Post Construction" (hereafter "the Chalifoux Patent");

8. U.S. Pat. No. 5,489,210 issued to Hanosh on Feb. 6, 1996 for "Expanding Dental Implant And Method For Its Use" (hereafter "the Hanosh Patent"); and 9. U.S. Pat. No. 5,533,898 issued to Mena on Jul. 9, 1996 for "Dental Implant Device" (hereafter "the Mena Patent").

The Detsch Patent discloses a dental implant attachment system. It comprises a base member which seats on the upper end of an implant cylindrical member embedded in the jawbone and a prosthetic head which is seated on the upper end of the base member. The prosthetic head forms a mount for seating a crown.

The Niznick Patent discloses an angled abutment for endosseous dental implants. The Otani Patent discloses a dental implant. It comprises a core material and a porous layer formed on the core material, where a portion of the core material is coated by the porous layer which has a non-circular cross-sectional shape so as not to rotate relative to the porous layer.

The Kirsch Patent discloses an enossal implant. It comprises a base member which is inserted in a prepared hole in the jawbone. The base member has an axial bore which receives a rigid inner sleeve. The rigid inner sleeve also has an axial bore which receives the implant post.

The Jorneus Patent discloses a distance member for a tooth implant anchored in the jaw. It comprises a sleeve shaped element which is connected with the shoulder part of the securing fixture of the tooth implant and a distance screw for engaging in a bore in the upper part of the fixture for anchoring the sleeve shaped element on the fixture.

The Sutter Patent discloses a device for fixing a dental prosthesis to a jawbone. It comprises a base, an abutment and a shell. The base has a hole with a mouth at its end face, with an internal thread and with an extension and has a conical annular surface enclosing the mouth of the hole.

The Chalifoux Patent discloses a dental implant and post construction. The post has a circumferential collar that mates with an upper portion of a circumferential wall of the implant. The circumferential collar resists expansion of the implant after being in a patient.

The Hanosh Patent discloses an expanding dental implant and method for its use.

The Mena Patent discloses a dental implant device. It comprises a root form implant fixture and an abutment member. The implant fixture has an anchorage section and an engagement section. The anchorage section has a shaft with threads, which section is inserted into the bone to occupy the space in between for anchoring the implant fixture.

It is always desirable to improve the anatomical restoration dental implant system which can provide a contour more nearly approximating that of a natural tooth and its surrounding tissue. It is also desirable to provide an anatomic implant with a matching abutment that enhances the resistance to bacterial infection.

SUMMARY OF THE INVENTION

The present invention is an anatomical restoration dental implant system for posterior and anterior teeth, which is embedded within a tapered alveolus of a patient's jawbone. The implant system comprises an anatomic implant fixture, a matching abutment member seated above the anatomic implant fixture and a bolt member for securing the abutment member to the anatomic implant fixture.

The implant fixture has a head section with a top end, a tapered shaft section with a bottom end, and an off-center stepped interior closed bore which extends downwardly from the top end to the middle of the tapered shaft section, the top end having a bevel periphery surface. When the teeth are large, the bone resorption progresses from facial side to the lingual side. The off-center alignment of the head section of the present invention implant fixture compensates this pattern of bone resorption.

The tapered shaft section of the implant fixture has a plurality of spaced apart transverse annular grooves and a longitudinal groove, where the plurality of spaced apart transverse annular grooves and the longitudinal groove provide a greater surface area into which bone growth are formed to prevent the implant fixture from vertical and rotational movements once the tapered shaft section has been press-fitted within the tapered alveolus of the jawbone. The bottom end of the shaft section has a gap therebetween for also allowing bone growth therein to prevent the implant fixture from rotational movements.

The head section and the shaft section of the implant fixture are integrally formed and connected as one-piece without any micro gap there between. This important feature prevents bacteria or other infection growth between the head section and the shaft section of the implant fixture. This one-piece implant fixture can also be used in both the one-stage and the two-stage implant surgeries.

The matching abutment member is used for supporting a tooth analogue. It has a proximal portion with a proximal end, a distal end with an opening, a stepped interior bore which extends from the distal end to the proximal end, the proximal end having a complementary interior bevel periphery surface surrounding the stepped interior bore. The abutment member is installed over the top end of the head section of the implant fixture such that the complementary interior bevel periphery surface of the abutment member abuts against the bevel periphery surface of the top end of the implant fixture, thereby providing a perfect match therebetween. The matching abutment can also have a pre-angulated shape to correct the misplaced implant fixture position.

The bolt member is inserted into the stepped interior bore of the abutment member and threadedly engaged with the inner threads of the off-center interior bore of the implant fixture, thereby securing the abutment member to the implant fixture.

It is therefore an object of the present invention to provide a dental implant fixture which has a plurality of transverse annular grooves and a longitudinal groove for providing a greater surface area into which bone growth are formed to prevent the implant fixture from vertical and rotational movements and to further support the implant fixture within the patient's jawbone.

It is another object of the present invention to provide a dental implant fixture where the head section and the shaft section of the implant fixture are integrally formed and connected as one-piece without any micro gap there between, to thereby prevent bacteria or other infection growth between the head section and the shaft section of the implant fixture.

It is an additional object of the present invention to provide a dental implant fixture with an arch shaped bottom end for also providing a surface area which bone growth is formed to prevent the implant fixture from further rotational movements.

It is a further object of the present invention to provide a dental implant fixture with various shaped top surfaces and a matching abutment member with various shaped bottom surfaces such as elliptical shapes or rounded triangle shapes, which can provide a better match with various shaped tooth analogues.

It is still a further object of the present invention to provide a dental implant fixture with a top end having a bevel periphery surface and a matching abutment member with a bottom end having a complementary bevel periphery surface to match the top bevel periphery surface of the implant fixture, which creates an emergence profile of the future crown.

In a first preferred embodiment, the present invention anatomical dental implant system is used for posterior teeth. It includes an implant fixture which has an elliptical shaped top surface with a bevel periphery surface, and an abutment member which has a matching elliptical shaped bottom surface which matches the elliptical shaped top surface of the implant fixture and a complementary bevel surface which matches the bevel periphery surface of the implant fixture.

In a second preferred embodiment, the present invention anatomical dental implant system is used for upper four front anterior teeth. It includes an implant fixture which has a rounded triangle shaped top surface with a bevel periphery surface, and an abutment member which has a matching rounded triangle shaped bottom surface which matches the rounded triangle top surface of the implant fixture and a complementary bevel surface which matches the bevel periphery surface of the implant fixture.

In a third preferred embodiment, the present invention anatomical dental implant system is used for lower four front anterior teeth. It includes an implant fixture which has a rounded triangle shaped top surface with a bevel periphery surface, where a hexagonal nut is integrally formed on the rounded triangle shaped top surface of the implant fixture, and an abutment member which has a matching rounded triangle shaped bottom surface which matches the rounded triangle shaped top surface of the implant fixture and a complementary bevel surface which matches the bevel periphery surface of the implant, where the abutment member further has a hexagonal recess which is installed over the hexagonal nut on the implant fixture.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figures 1, 2:
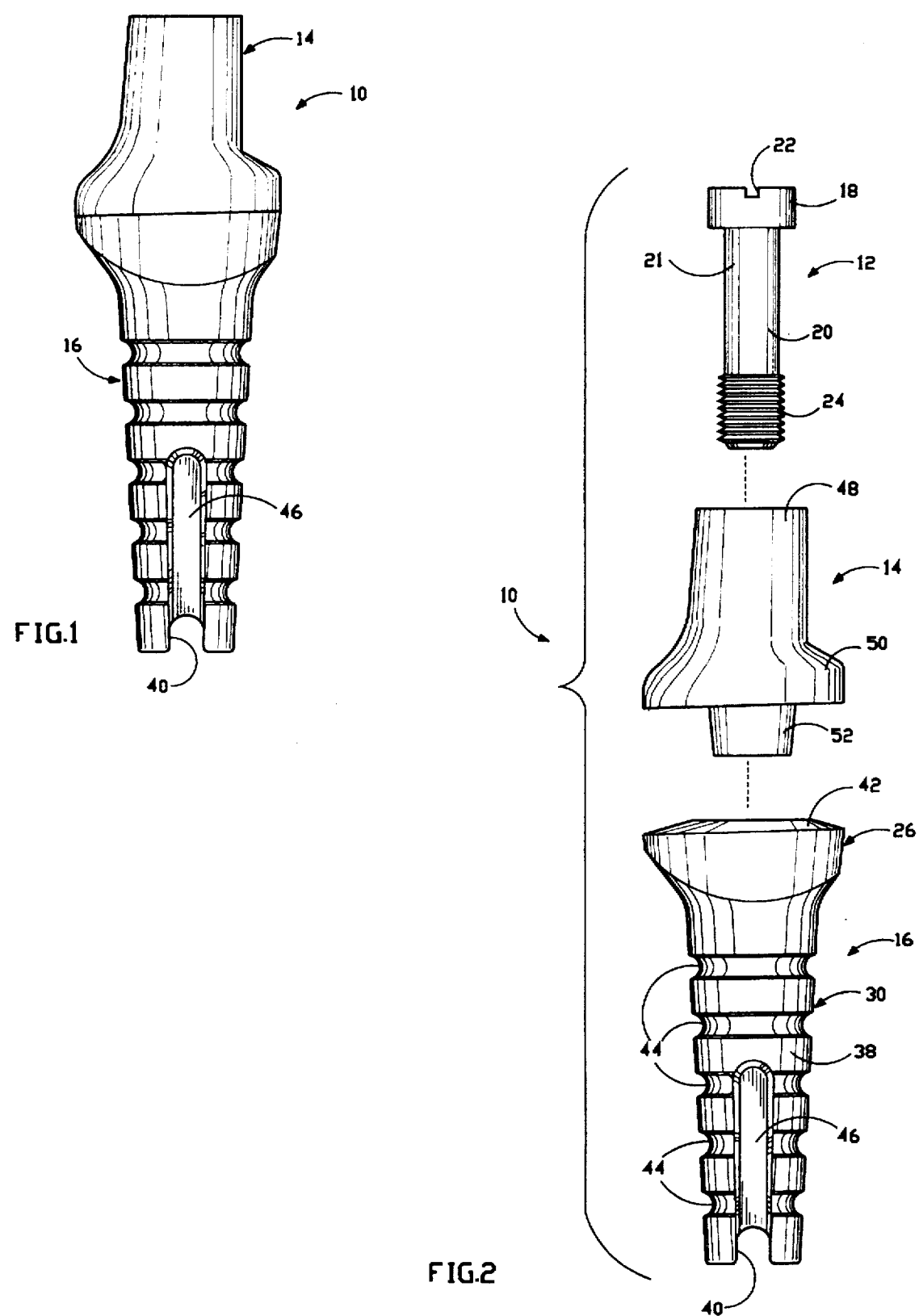
FIG. 1 is a side elevational view of a first preferred embodiment of the present invention anatomical restoration dental implant system for posterior teeth.
FIG. 2 is an exploded side elevational view of the present invention anatomical restoration dental implant system shown in FIG. 1.
Figure 3:
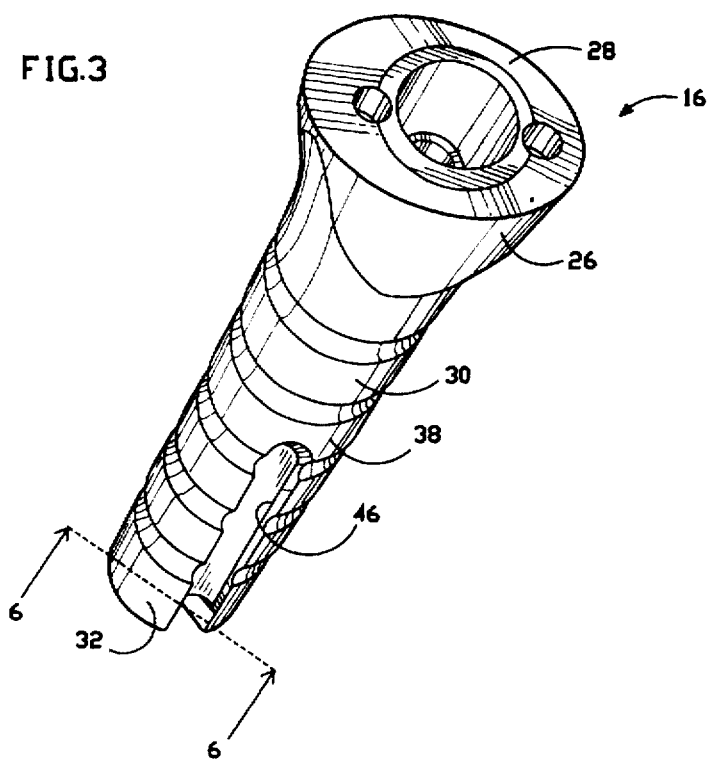
FIG. 3 is a perspective view of an anatomic dental implant fixture of the present invention anatomical restoration dental implant system shown in FIG. 1.

Referring to FIGS. 1 and 2, there are shown respective side elevational view and exploded side elevational view of the first preferred embodiment of the present invention anatomical restoration dental implant system 10 for posterior teeth, including a small bolt member 12, a matching abutment member 14, and an anatomic dental implant fixture 16. The dental implant fixture 16 is embedded into a tapered alveolus 8 which is surgically provided in a patient's jawbone 2 (see FIG. 11 ).

Referring to FIG. 2, the bolt member 12 has a widened head segment 18 and an elongated shaft segment 20. The widened head segment 18 is generally disc shaped with a top notch or cross notch 22 or any other suitable means to accommodate a driving tool, for example, a screwdriver or any other tool for rotating the bolt member 12. The shaft segment 20 has one end 21 integrally connected to the head segment 18. The shaft segment 20 has outer screw threads 24 which are located opposite from the head segment 18 and extend along at least a portion of its length.

Referring to FIGS. 1, 2, 3 and 5, the anatomic dental implant fixture 16 consists of a head section 26 with a widened proximal end 28 and an elongated tapered shaft section 30 with a narrow distal end 32. The head section 26 is integrally connected to the tapered shaft section 30, and thereby forms a one-piece implant fixture 16. This prevents bacteria or other infection growth between the head section and the shaft section of the implant fixture.

The implant fixture 16 further has an off-center stepped interior closed bore 36 which extends partially downward from the widened proximal end 28 to the middle 38 of the tapered shaft section 30. The interior closed bore 36 has inner screw threads 45 along at least a portion of its length and an annular shelf 43 located above the inner screw threads 45 (see FIG. 5).

Figure 4:
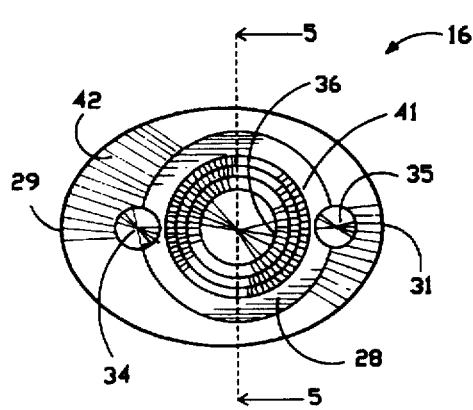
FIG. 4 is an enlarged top plan view of the anatomic dental implant fixture of the present invention anatomical restoration dental implant system shown in FIG. 3, showing an elliptical shaped surface.
Figure 6:
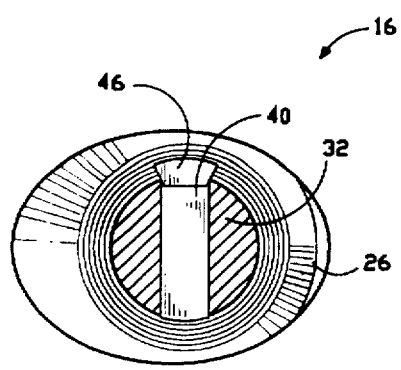
FIG. 6 is an enlarged bottom plan view of the anatomic dental implant fixture of the present invention anatomical restoration dental implant system shown in FIG. 3.
Figure 7:
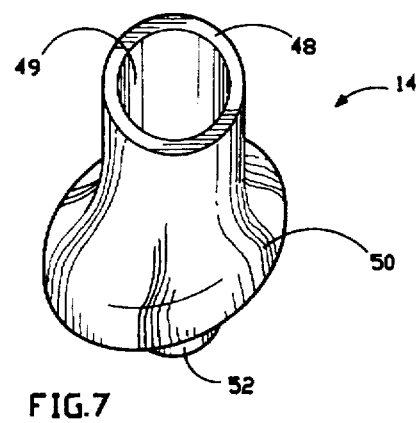
FIG. 7 is a perspective view of a matching abutment member of the present invention anatomical restoration dental implant system shown in FIG. 1.

Referring to FIGS. 4 and 6, there are shown respective enlarged top and bottom plan views of the anatomic implant fixture 16. The narrow distal end 32 is generally circular shaped with an arch shaped gap 40, whereas the widened proximal end 28 is generally elliptical shaped. The elliptical shaped proximal end 28 has a circular flat surface 41 surrounded by a bevel periphery surface 42 and has a long-axis and a short axis. The elliptical proximal end 28 further has two small opposite closed apertures 34 and 35 for accommodating small tips of a standard dental tool, for example, a forceps for orienting the implant fixture 16. The head section 26 also has a wider facial-side surface area 29 and a narrower lingual-side surface area 31. The facial-side surface area 29 accommodates the contour of the gingival tissue at the facial-side of the patient's oral cavity, which is located adjacent to the interior surface of the patient's cheek, while the lingual-side surface area 31 accommodates the contour of the gingival tissue at the lingual-side of the patient's oral cavity which is located adjacent to the patient's tongue.

Figure 5:
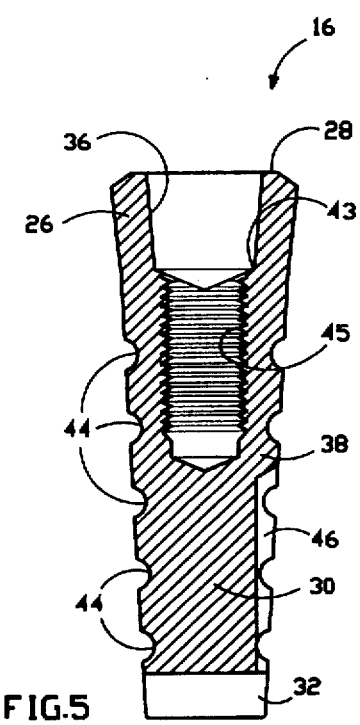
FIG. 5 is a cross-sectional view taken along line 5—5 of FIG. 4.
Figure 11:
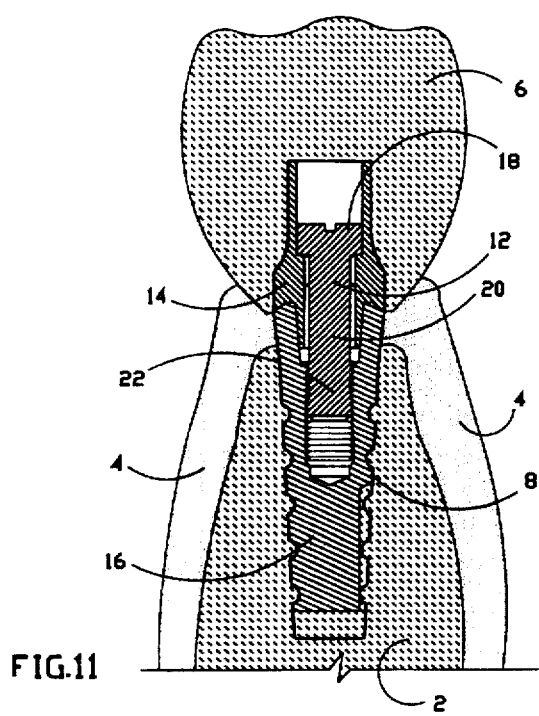
FIG. 11 is a cross-sectional view, showing the matching abutment member secured on top of the dental implant fixture for supporting a tooth analogue.

Referring to FIGS. 5 and 11, the tapered shaft section 30 of the implant fixture 16 has a plurality of spaced apart transverse annular grooves 44 and a longitudinal groove 46. The longitudinal groove 46 extends upwardly from the narrow distal end 32 to the middle 38 of the tapered shaft section 30, where the plurality of transverse annular grooves 44 and the longitudinal groove 46 provide a greater surface area into which bone growth are formed to prevent the implant fixture 16 from vertical and rotational movements within the jawbone 2. The gap 40 at the narrow distal end 32 of the tapered distal shaft section 30 further provides an area, where bone growth can grow therein to prevent the implant fixture 16 from further rotational movements. The tapered shaft section 30 of the implant fixture 16 is installed within the tapered alveolus 8 of the jawbone 2 by press-fit such that the head section 26 rests above the jawbone 2. The head section 26 of the implant fixture 16 has a generally divergent shaped body for accommodating the gingival tissues 4 which surround the patient's jawbone 2. The implant fixture 16 is oriented within the tapered alveolus 8 of the jawbone 2 by rotating the head section 26 so that the facial side area 29 is located adjacent to the interior surface of the patient's oral cavity while the lingual-side area 31 is located adjacent to the patient's tongue.

Referring to FIG. 1, 2, 7, 9 and 11, the matching abutment member 14 is used for supporting a tooth analogue 6. The tooth analogue 6 may be attached to the abutment member 14 by conventional means such as cement or a small screw (not shown) which can be inserted from the side of tooth analogue 6 and threaded into the abutment member 14. The abutment member 14 has a narrow distal end 48 with a circular opening 49, a widened proximal portion 50 with a protruding proximal truncated cone shaped engagement end 52 extending therefrom, and a stepped interior bore 54 which extends through from the distal end 48 to the protruding proximal truncated cone shaped engagement end 52.

Figure 8:
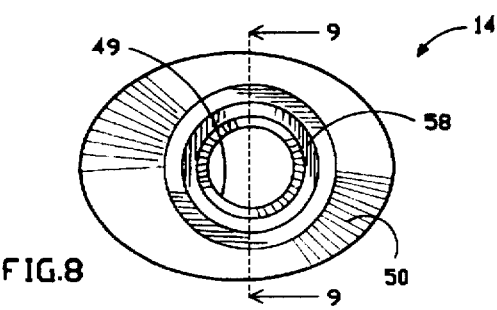
FIG. 8 is an enlarged top plan view of the matching abutment member of the present invention anatomical restoration dental implant system shown in FIG. 7.
Figure 10:
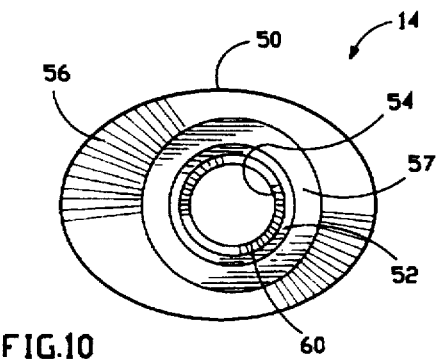
FIG. 10 is an enlarged bottom plan view of the matching abutment member of the present invention anatomical restoration dental implant system shown in FIG. 7.

Referring to FIGS. 8 and 10, there are shown respective enlarged top and bottom plan views of the abutment member 14. The widened proximal portion 50 is generally elliptical shaped which matches the widened elliptical shaped proximal end 28 of the head section 26 of the implant fixture 16. The elliptical shaped proximal portion 50 further has an interior circular flat surface 57 surrounding the protruding engagement end 52. The interior circular flat surface 57 is surrounded by an interior bevel periphery surface 56. These surfaces 57 and 56 of the abutment member 14 respectively match the surfaces 41 and 42 of the head section 26 of the implant fixture 16.

Referring to FIGS. 1 and 11, the abutment member 14 is seated over the implant fixture 16 by inserting the protruding engagement end 52 into the off-center interior bore 36 of the implant fixture 16, where the elliptical shaped proximal portion 50 of the abutment member 14 matches and completed covers the elliptical shaped proximal end 28 of the head section 26 of the implant fixture 16. It can be seen that the bevel periphery surface 42 of the head section 26 of the implant fixture 16 now matches perfectly with the interior bevel periphery surface 56 of the abutment member 14. As shown in FIGS. 1 and 11, the elliptical shaped proximal portion 50 of the abutment member 14 fully covers the elliptical shaped proximal end 28 of head section 26 of the implant fixture 16. This eliminates any possibility of having food debris and bacteria collected between the abutment member 14 and the dental implant fixture 16 and reduces the chance of causing any infectious diseases.

Referring now to FIG. 11, the abutment member 14 is seated and secured to the dental implant fixture 16 by the bolt member 12. The bolt member 12 is inserted into the stepped interior bore 54 of the abutment member 14 from the opening 49 at the narrow distal end 48 of the abutment member 14, where the head segment 18 rests on a shelf 58 (see FIG. 9) provided within the interior bore 54. The outer threads 24 on the shaft segment 20 of the bolt member 12 are compatible with the inner screw threads 45 of the implant fixture 16. It is noted that the shaft segment 20 of the bolt member 12 is longer than the stepped interior bore 54 of the abutment member 14, so that after the shaft segment 20 of the bolt member 12 extends through the interior bore 54 of the abutment member 14, there is still a substantial length of the shaft segment 20 of the bolt member 12 which can be threadably engaged with the inner screw threads 45 of the dental implant fixture 16 for fastening the abutment member 14 thereupon.

Figure 9:
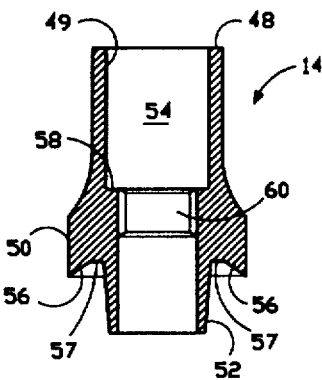
FIG. 9 is a cross-sectional view taken along line 9—9 of FIG. 8.

Referring to FIG. 9, the stepped interior bore 54 of the abutment member 14 may further include inner screw threads 60 which are compatible with the outer screw threads 24 of the shaft segment 20 of the bolt member 12. The inner screw threads 60 are located adjacent to and below the shelf 58. This provides an interlocked feature, in which the abutment member 14 and the bolt member 12 can be handled together as a unit, which reduces the possibility of either dropping or losing the small bolt member 12.

The present invention restoration dental implant system 10 may further include another small bolt member (not shown) for temporary covering the off-center stepped interior closed bore 36 of the implant fixture 16. This small bolt member may be threadedly engaged the inner screw threads 45, where the head of the small bolt member will be flush with the circular flat surface 41 of the head section 26 of the implant fixture and rests on the annular shelf 43, so that the healed gingival tissues around the tooth will not growth within the off-center interior closed bore 36.

The anatomical restoration dental implant system 10 further reduces the possibility of mismatching pairs of different configurations or dimensions of the implant fixtures and the matching abutment members, because the bottom configuration of the matching abutment member 14 and the top configuration of the implant fixture 16 are complementary of one another. The smaller profile of the widened elliptical proximal end of the implant fixture 16 also allows two tooth analogues to be positioned at a desired or required close distance.

Figure 12:
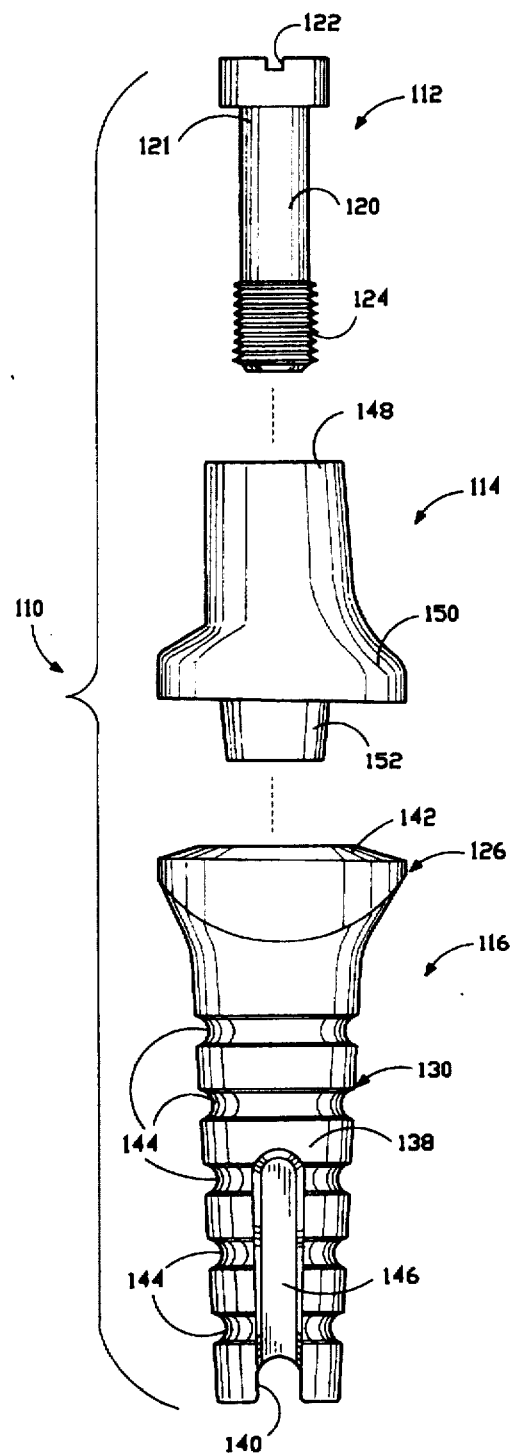
FIG. 12 is an exploded side elevational of a second preferred embodiment of the present invention anatomical restoration dental implant system for the upper four front anterior teeth.

Referring to FIG. 12, there is shown an exploded side elevational view of a second preferred embodiment of the present invention anatomical restoration dental implant system 110 for the upper four front anterior teeth, including a small bolt member 112, a matching abutment member 114, and an anatomic dental implant fixture 116. Since the anatomical restoration dental implant system 110 assembles and functions the same as previously described above except that the rounded equilateral triangle shaped proximal end 128 of the head section 126 of the implant fixture 116 and the rounded equilateral triangle shaped proximal portion 150 of the abutment member 114 are respectively substituted for the elliptical shaped proximal end 28 of the head section 26 of the implant fixture 16 and the elliptical shaped proximal portion 50 of the abutment member 14 shown in FIGS. 1 through 11, their parts are numbered correspondingly with 100 added to each reference number.

The bolt member 112 has a widened head segment 118 and an elongated shaft segment 120. The widened head segment 118 is generally disc shaped with a top notch or cross notch 122 or any other suitable means to accommodate a driving tool, for example, a screwdriver or any other tool for rotating the bolt member 112. The shaft segment 120 has one end 121 integrally connected to the head segment 118. The shaft segment 120 has outer screw threads 124 which are located opposite from the head segment 118 and extend along at least a portion of its length.

Figure 15:
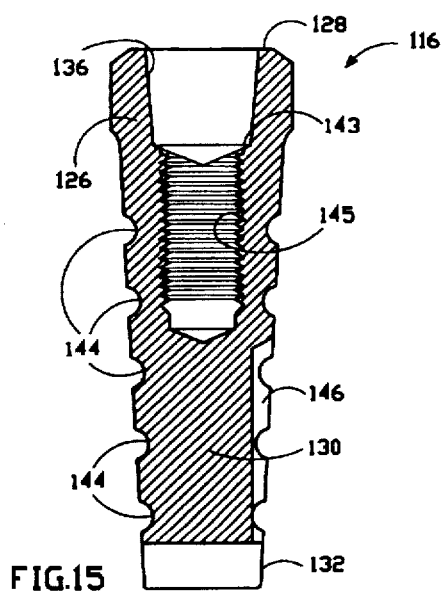
FIG. 15 is a cross-sectional view taken along line 15—15 of FIG. 14.
Figure 13:
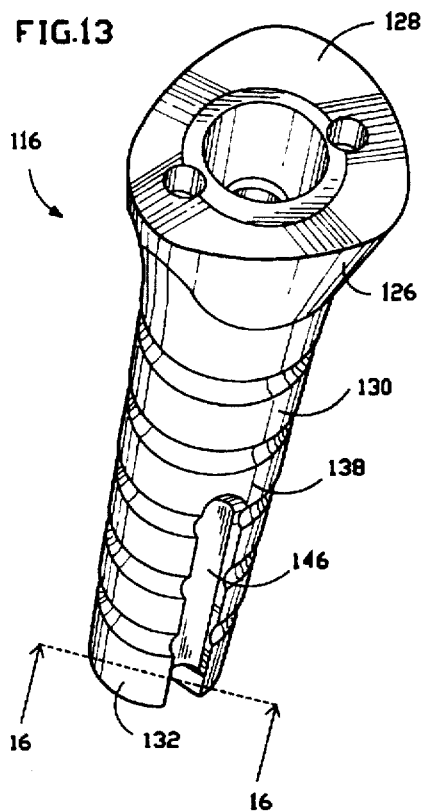
FIG. 13 is a perspective view of an anatomic dental implant fixture of the present invention anatomical restoration dental implant system shown in FIG. 12.

Referring to FIGS. 12, 13 and 15, the anatomic dental implant fixture 116 consists of a head section 126 with a widened proximal end 128 and an elongated tapered shaft section 130 with a narrow distal end 132. The head section 126 is integrally connected to the tapered shaft section 130, and thereby forms the anatomic dental implant fixture 116. The implant fixture 116 further has an off-center stepped interior closed bore 136 which extends partially downward from the widened proximal end 128 to the middle 138 of the tapered shaft section 130. The interior closed bore 136 has inner screw threads 145 along at least a portion of its length and an annular shelf 143 located above the inner screw threads 45 (see FIG. 15).

Figure 14:
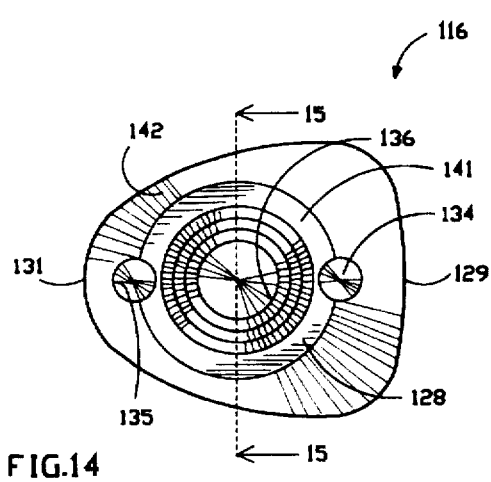
FIG. 14 is an enlarged top plan view of the anatomic dental implant fixture of the present invention anatomical restoration dental implant system shown in FIG. 13, showing a rounded equilateral triangle shaped surface.
Figure 16:
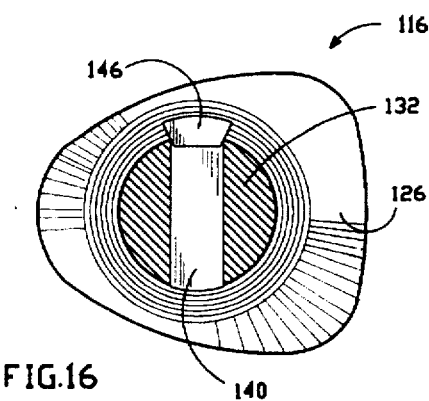
FIG. 16 is an enlarged bottom plan view of the anatomic dental implant fixture of the present invention anatomical restoration dental implant system shown in FIG. 13.

Referring to FIGS. 14 and 16, there are shown respective enlarged top and bottom plan views of the anatomic implant fixture 116. The narrow distal end 132 is generally circular shaped with an arch shaped gap 140, whereas the widened proximal end 128 is generally rounded triangle shaped. The rounded triangle shaped proximal end 128 has a circular flat surface 141 surrounded by a bevel periphery surface 142. The rounded triangle shaped proximal end 128 further has two small opposite closed apertures 134 and 135 for accommodating small tips of a standard dental tool. The head section 126 also has a wider facial-side surface area 129 and a narrower lingual-side surface area 131. The facial-side surface area 129 accommodates the contour of the gingival tissue at the facial-side of the patient's oral cavity, while the lingual-side surface area 131 accommodates the contour of the gingival tissue at the lingual-side of the patient's oral cavity which is located adjacent to the patient's tongue.

Referring to FIGS. 12, 13 and 15, the tapered shaft section 130 of the implant fixture 116 has a plurality of spaced apart transverse annular grooves 144 and a longitudinal groove 146. The longitudinal groove 146 extends upwardly from the narrow distal end 132 to the middle 138 of the tapered shaft section 130, where the plurality of transverse annular grooves 144 and the longitudinal groove 146 provide a greater surface area into which bone growth are formed to prevent the implant fixture 116 from vertical and rotational movements within the jawbone. The gap 140 at the narrow distal end 132 of the tapered distal shaft section 130 further provides an area, where bone growth can grow therein to prevent the implant fixture 116 from further rotational movements. The tapered shaft section 130 of the implant fixture 116 is installed within the tapered alveolus of the jawbone by press-fit such that the head section 126 rests above the jawbone. The head section 126 of the implant fixture 116 has a generally divergent shaped body for accommodating the gingival tissues which surround the patient's jawbone. The implant fixture 116 is oriented within the tapered alveolus of the jawbone by rotating the head section 126.

Figure 17:
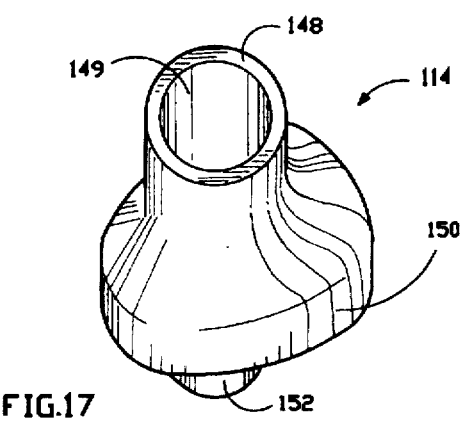
FIG. 17 is a perspective view of the matching abutment member of the present invention anatomical restoration dental implant system shown in FIG. 12.
Figure 19:
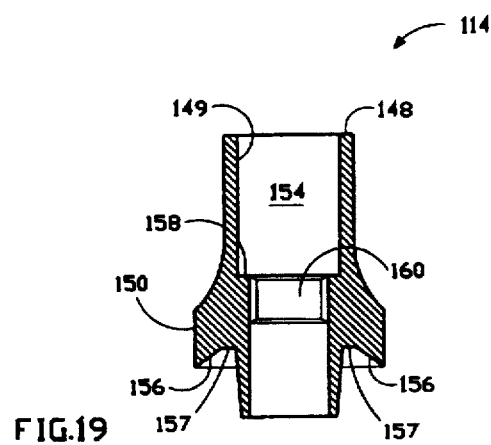
FIG. 19 is a cross-sectional view taken along line 19—19 of FIG. 18.

Referring to FIG. 12, 17 and 19, the matching abutment member 114 is used for supporting a tooth analogue. The tooth analogue may be attached to the abutment member 114 by conventional means such as cement or a small screw (not shown) which can be inserted from the side of tooth analogue and threaded into the abutment member 114. The abutment member 114 has a narrow distal end 148 with a circular opening 149, a widened proximal portion 150 with a protruding proximal truncated cone shaped engagement end 152 extending therefrom, and a stepped interior bore 154 which extends through from the distal end 148 to the protruding proximal truncated cone shaped engagement end 152.

Figure 18:
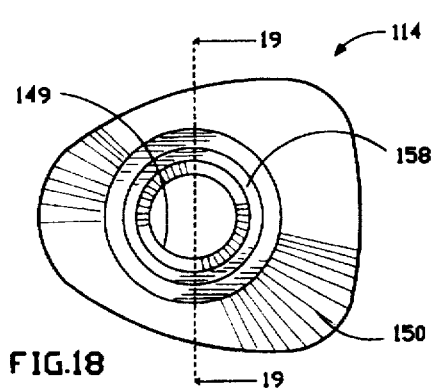
FIG. 18 is an enlarged top plan view of the matching abutment member of the present invention anatomical restoration dental implant system shown in FIG. 17.
Figure 20:
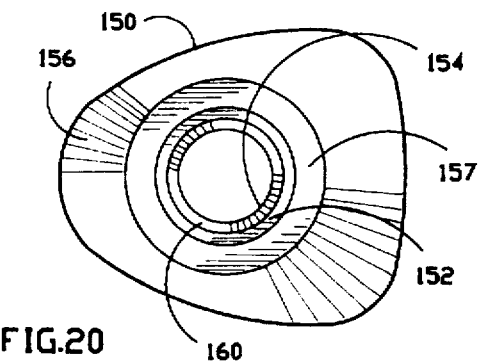
FIG. 20 is an enlarged bottom plan view of the matching abutment member of the present invention anatomical restoration dental implant system shown in FIG. 17.
Figure 23:
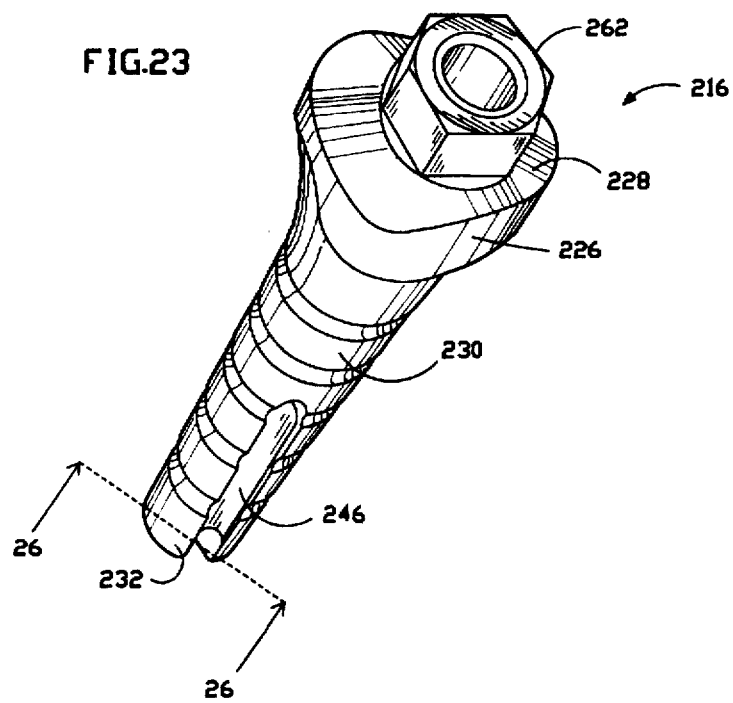
FIG. 23 is a perspective view of an anatomic dental implant fixture of the present invention anatomical restoration dental implant system shown in FIG. 21.

Referring to FIGS. 18 and 20, there are shown respective enlarged top and bottom plan views of the abutment member 114. The widened proximal portion 150 is generally rounded equilateral triangle shaped which matches the rounded equilateral triangle shaped proximal end 128 of the head section 126 of the implant fixture 116. The rounded equilateral triangle shaped proximal portion 150 further has an interior circular flat surface 157 surrounding the protruding engagement end 152. The interior circular flat surface 157 is surrounded by an interior bevel periphery surface 156. These surfaces 157 and 156 of the abutment member 114 respectively match the surfaces 141 and 142 of the head section 126 of the implant fixture 116.

Referring again to FIG. 12, the abutment member 114 is seated over the implant fixture 116 by inserting the protruding engagement end 152 into the off-center interior bore 136 of the implant fixture 116, where the rounded triangle shaped proximal portion 150 of the abutment member 114 matches and completed covers the rounded triangle shaped proximal end 128 of the head section 126 of the implant fixture 116. It can be seen that the bevel periphery surface 142 of the head section 126 of the implant fixture 116 now matches perfectly with the interior bevel periphery surface 156 of the abutment member 114. The rounded equilateral triangle shaped proximal portion 150 of the abutment member 114 fully covers the rounded equilateral triangle shaped proximal end 128 of head section 126 of the implant fixture 116. This eliminates any possibility of having food debris and bacteria collected between the abutment member 114 and the dental implant fixture 116 and reduces the chance of causing any infectious diseases.

The abutment member 114 is seated and secured to the dental implant fixture 116 by the bolt member 112. The bolt member 112 is inserted into the stepped interior bore 154 of the abutment member 114 from the opening 149 at the narrow distal end 148 of the abutment member 114, where the head segment 118 rests on a shelf 158 provided within the interior bore 154. It is noted that the shaft segment 120 of the bolt member 112 is longer than the stepped interior bore 154 of the abutment member 114, so that after the shaft segment 120 of the bolt member 112 extends through the interior bore 154 of the abutment member 114, there is still a substantial length of the shaft segment 120 of the bolt member 112 which can be threadably engaged with the inner screw threads 145 of the dental implant fixture 116 for fastening the abutment member 114 thereupon.

Referring to FIG. 19, the stepped interior bore 154 of the abutment member 114 may further include inner screw threads 160 which are compatible with the outer screw threads 124 of the shaft segment 120 of the bolt member 112. The inner screw threads 160 are located adjacent to and below the shelf 158. This provides an interlocked feature, in which the abutment member 114 and the bolt member 112 can be handled together as a unit, which reduces the possibility of either dropping or losing the small bolt member 112.

The present invention restoration dental implant system 110 may further include another small bolt member (not shown) for temporary covering the off-center stepped interior closed bore 136 of the implant fixture 116. This small bolt member will threadedly engaged the inner screw threads 145, where the head of the small bolt member will be flush with the circular flat surface 141 of the head section 126 of the implant fixture 116 and rests on the annular shelf 143, so that the healed gingival tissues around the tooth will not growth within the off-center interior closed bore 136.

Figure 21:
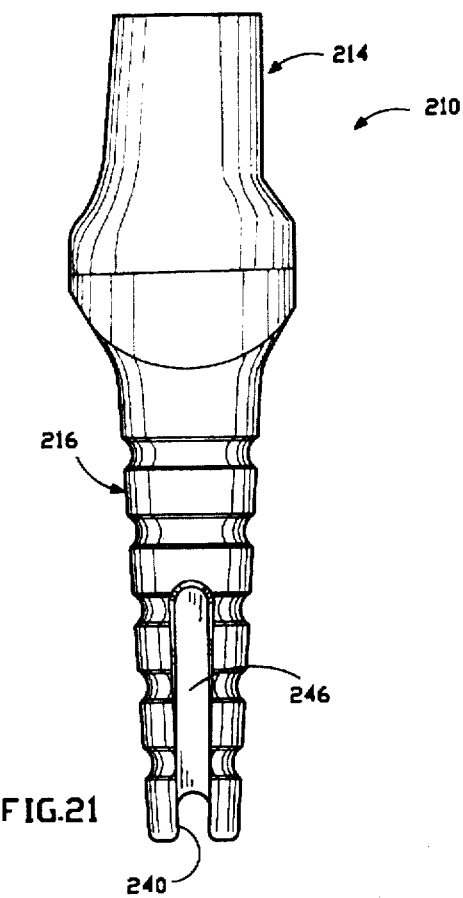
FIG. 21 is a side elevational view of a third preferred embodiment of the present invention anatomical restoration dental implant system for the lower four front anterior teeth.
Figure 22:
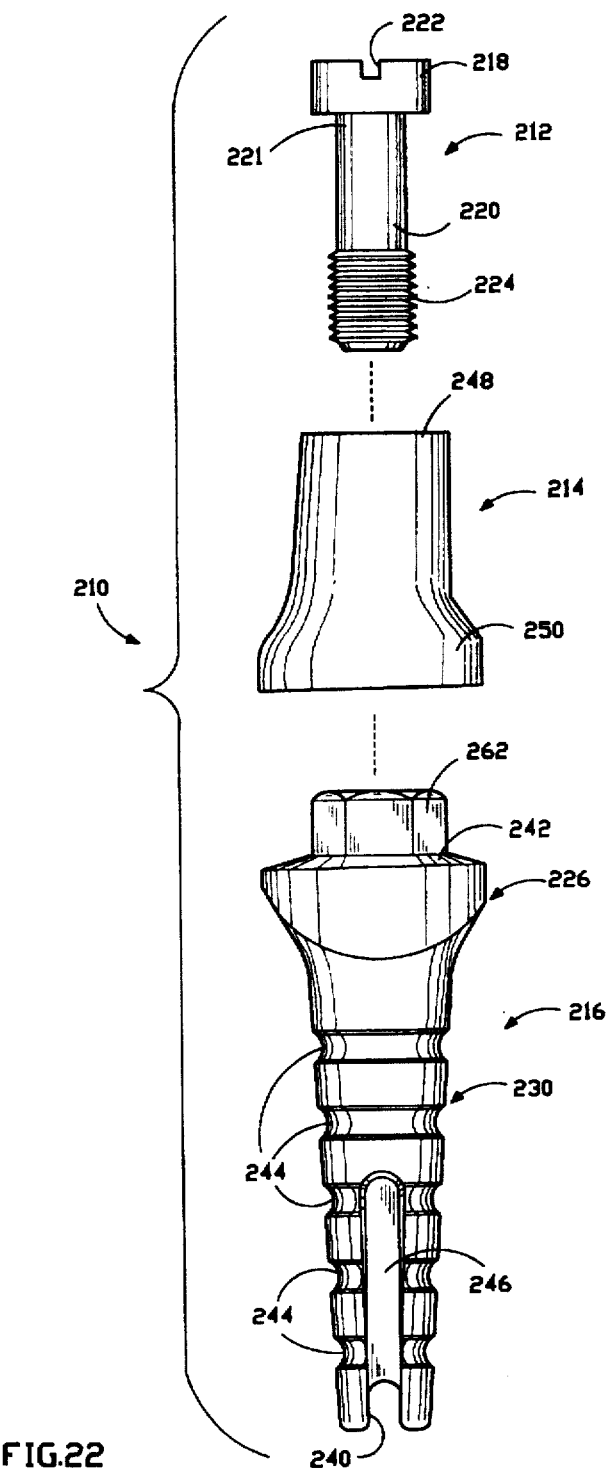
FIG. 22 is an exploded side elevational view of the present invention anatomical restoration dental implant system shown in FIG. 21.

Referring to FIGS. 21 and 22, there are shown respective side elevational view and exploded side elevational view of a third preferred embodiment of the present invention anatomical restoration dental implant system 210 for the lower four front anterior teeth, including a small bolt member 212, a matching abutment member 214, and an anatomic dental implant fixture 216. Since the anatomical restoration dental implant system 210 assembles and functions the same as previously described in FIGS. 1 through 11 except that the rounded isosceles triangle shaped proximal end 228 of the head section 226 of the implant fixture 216 and the rounded isosceles triangle shaped proximal portion 250 of the abutment member 214 are respectively substituted for the elliptical shaped proximal end 28 of the head section 26 of the implant fixture 16 and the elliptical shaped proximal portion 50 of the abutment member 14, their parts are numbered correspondingly with 200 added to each reference number.

Referring to FIG. 22, the bolt member 212 has a widened head segment 218 and an elongated shaft segment 220. The widened head segment 218 is generally disc shaped with a top notch or cross notch 222 or any other suitable means to accommodate a driving tool, for example, a screwdriver or any other tool for rotating the bolt member 212. The shaft segment 220 has one end 221 integrally connected to the head segment 218. The shaft segment 220 has outer screw threads 224 which are located opposite from the head segment 218 and extend along at least a portion of its length.

Referring to FIGS. 21, 22, 23 and 25, the anatomic dental implant fixture 216 consists of a head section 226 with a widened proximal end 228 and an elongated tapered shaft section 230 with a narrow distal end 232. The head section 226 is integrally connected to the tapered shaft section 230. A hexagonal shaped nut 262 is integrally formed on the widened proximal end 228 of the head section 226. The implant fixture 216 further has an off-center interior closed bore 236 which extends partially downward from the hexagonal shaped nut 262 to the middle 238 of the tapered shaft section 230. The interior closed bore 236 has inner screw threads 245.

Figure 24:
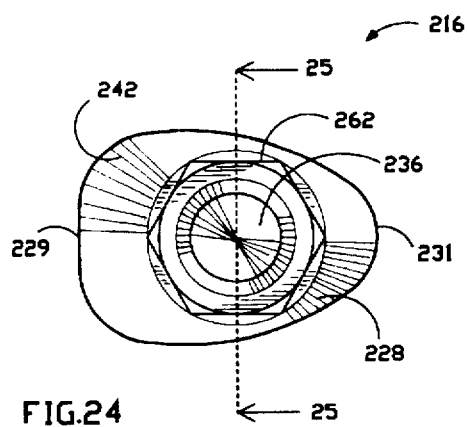
FIG. 24 is an enlarged top plan view of the anatomic dental implant fixture of the present invention anatomical restoration dental implant system shown in FIG. 23, showing a rounded isosceles triangle shaped surface.
Figure 26:
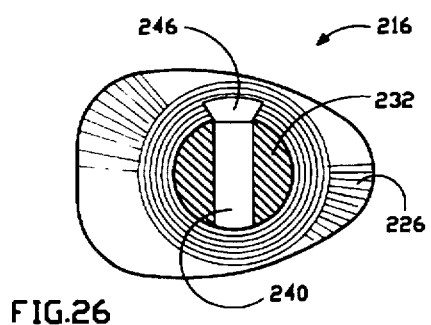
FIG. 26 is an enlarged bottom plan view of the anatomic dental implant fixture of the present invention anatomical restoration dental implant system shown in FIG. 23.
Figure 27:
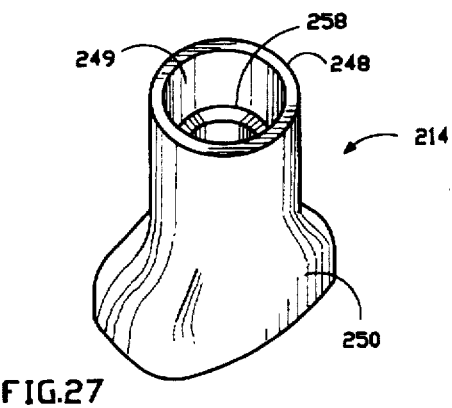
FIG. 27 is a perspective view of a matching abutment member of the present invention anatomical restoration dental implant system shown in FIG. 21.

Referring to FIGS. 24 and 26, there are shown respective enlarged top and bottom plan views of the anatomic implant fixture 216. The narrow distal end 232 is generally circular shaped with an arch shaped gap 240, whereas the widened proximal end 28 is generally rounded isosceles triangle shaped. The rounded isosceles triangle shaped proximal end 228 has a bevel periphery surface 242. The head section 226 also has wider facial-side surface area 229 and a narrower lingual-side surface area 231. The facial-side surface area 229 accommodates the contour of the gingival tissue at the facial-side of the patient's oral cavity, while the lingual-side surface area 231 accommodates the contour of the gingival tissue at the lingual-side of the patient's oral cavity which is located adjacent to the patient's tongue.

Figure 25:
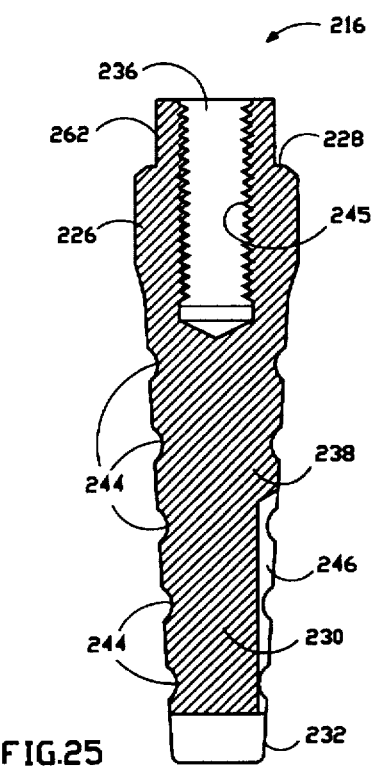
FIG. 25 is a cross-sectional view taken along line 25—25 of FIG. 24.
Figure 31:
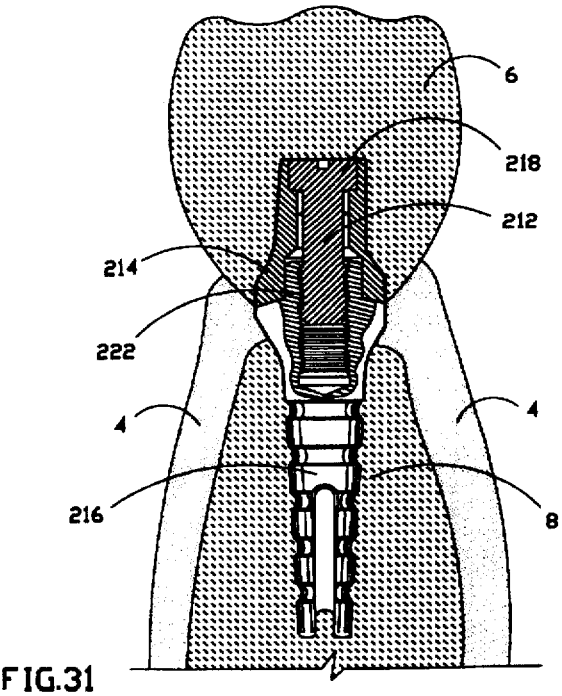
FIG. 31 is a partial cross-sectional view, showing the matching abutment member secured on top of the dental implant fixture for supporting a tooth analogue.

Referring to FIGS. 25 and 31, the tapered shaft section 230 of the implant fixture 216 has a plurality of spaced apart transverse annular grooves 244 and a longitudinal groove 246. The longitudinal groove 246 extends upwardly from the narrow distal end 232 to the middle 238 of the tapered shaft section 230, where the plurality of transverse annular grooves 244 and the longitudinal groove 246 provide a greater surface area into which bone growth are formed to prevent the implant fixture 216 from vertical and rotational movements within the jawbone 2. The gap 240 at the narrow distal end 232 of the tapered distal shaft section 230 further provides an area, where bone growth can grow therein to prevent the implant fixture 216 from further rotational movements. The tapered shaft section 230 of the implant fixture 216 is installed within the tapered alveolus 8 of the jawbone 2 by press-fit such that the head section 226 rests above the jawbone 2 (see FIG. 31). The head section 226 of the implant fixture 216 has a generally divergent shaped body for accommodating the gingival tissues 4 which surround the patient's jawbone 2.

Referring to FIG. 21, 22, 27, 29 and 31, the matching abutment member 214 is used for supporting a tooth analogue 6. The tooth analogue 6 may be attached to the abutment member 214 by conventional means such as cement or a small screw (not shown) which can be inserted from the side of tooth analogue 6 and threaded into the abutment member 214. The abutment member 214 has a narrow distal end 248 with a circular opening 249, a widened proximal portion 250 with a proximal hexagonal recess 264, and a stepped interior bore 254 which extends through from the distal end 248 to the proximal hexagonal shaped recess 264.

Figure 28:
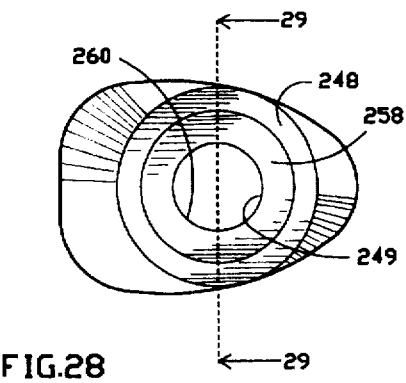
FIG. 28 is an enlarged top plan view of the matching abutment member of the present invention anatomical restoration dental implant system shown in FIG. 27.
Figure 30:
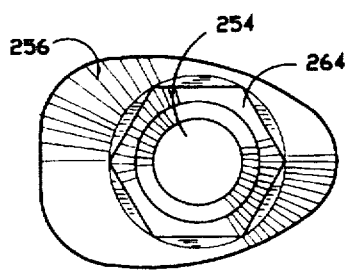
FIG. 30 is an enlarged bottom plan view of the matching abutment member of the present invention anatomical restoration dental implant system shown in FIG. 27.

Referring to FIGS. 28 and 30, there are shown respective enlarged top and bottom plan views of the abutment member 214. The widened proximal portion 250 is generally rounded isosceles triangle shaped which matches the rounded isosceles shaped proximal end 228 of the head section 226 of the implant fixture 216. The rounded isosceles shaped proximal portion 250 further has an interior bevel periphery surface 256. The bevel periphery surface 256 of the abutment member 214 matches the bevel periphery surface 242 of the head section 226 of the implant fixture 216.

Referring to FIGS. 21 and 31, the abutment member 114 is seated over the implant fixture 116 such that the hexagonal shaped recess 264 engages and covers the hexagonal shaped nut 262 of the implant fixture 216 and the rounded isosceles triangle shaped proximal portion 250 of the abutment member 214 matches and completed covers the rounded isosceles triangle shaped proximal end 228 of the head section 226 of the implant fixture 216. It can be seen that the bevel periphery surface 242 of the head section 226 of the implant fixture 216 now matches perfectly with the interior bevel periphery surface 256 of the abutment member 214. As shown in FIGS. 21 and 31, the rounded isosceles triangle shaped proximal portion 250 of the abutment member 214 fully covers the rounded isosceles shaped proximal end 228 of head section 226 of the implant fixture 216. This eliminates any possibility of having food debris and bacteria collected between the abutment member 214 and the dental implant fixture 216 and reduces the chance of causing any infectious diseases.

Referring now to FIG. 31, the abutment member 214 is seated and secured to the dental implant fixture 216 by the bolt member 212. The bolt member 212 is inserted into the stepped interior bore 254 of the abutment member 214 from the opening 249 at the narrow distal end 248 of the abutment member 214, where the head segment 218 rests on a shelf 258 provided within the interior bore 254. The outer threads 224 on the shaft segment 220 of the bolt member 212 are compatible with the inner screw threads 245 of the implant fixture 216. It is noted that the shaft segment 220 of the bolt member 212 is longer than the stepped interior bore 254 of the abutment member 214, so that after the shaft segment 220 of the bolt member 212 extends through the interior bore 254 of the abutment member 214, there is still a substantial length of the shaft segment 220 of the bolt member 212 which can be threadably engaged with the inner screw threads 245 of the dental implant fixture 216 for fastening the abutment member 214 thereupon.

Figure 29:
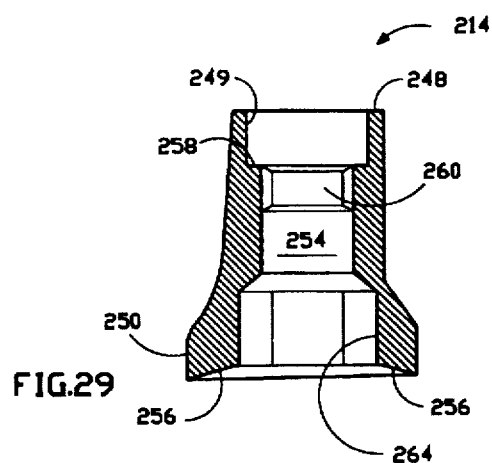
FIG. 29 is a cross-sectional view taken along line 29—29 of FIG. 28.

Referring to FIG. 29, the stepped interior bore 254 of the abutment member 214 may further include inner screw threads 260 which are compatible with the outer screw threads 224 of the shaft segment 220 of the bolt member 212. The inner screw threads 260 are located adjacent to and below the shelf 258. This provides an interlocked feature, in which the abutment member 214 and the bolt member 212 can be handled together as a unit, which reduces the possibility of either dropping or losing the small bolt member 212.

The present invention restoration dental implant system 10 may further include a cover cap (not shown) for temporary covering the hexagonal shaped nut 262 and the rounded isosceles triangle shaped proximal end 228 of the implant fixture 216, so that the healed gingival tissues around the tooth will not growth within the off-center interior closed bore 236.

Defined in detail, the present invention is an anatomic dental implant fixture for posterior teeth and implantable in a tapered alveolus of a patient's jawbone, the implant fixture comprising: (a) an implantable body having an elongated tapered shaft section with a narrow distal end, a divergent head section with a widened proximal end, and an off-center stepped interior closed bore extending downwardly from the widened proximal end to the middle of the tapered shaft section, the widened proximal end having an elliptical shape with a bevel periphery surface, the interior closed bore having inner screw threads; (b) said tapered shaft section of said implantable body being press-fitted within said tapered alveolus of said jawbone such that said divergent head section rests above said jawbone, said tapered shaft section having a plurality of spaced apart transverse annular grooves and a longitudinal groove extending upwardly from said narrow distal end to the middle of said tapered shaft section, where the plurality of spaced apart transverse annular grooves and the longitudinal groove provide a greater surface area into which bone growth are formed to prevent said implantable body from vertical and rotational movements within said jawbone; and (c) said narrow distal end of said tapered shaft section of said implantable body having an arch shaped gap for allowing bone growth therein to further prevent said implantable body from rotational movements.

Defined alternatively in detail, the present invention is an anatomic dental implant fixture for upper anterior teeth and implantable in a tapered alveolus of a patient's jawbone, the implant fixture comprising: (a) an implantable body having an elongated tapered shaft section with a narrow distal end, a divergent head section with a widened proximal end, and an off-center stepped interior closed bore extending downwardly from the widened proximal end to the middle of the tapered shaft section, the widened proximal end having a generally rounded equilateral triangle shape with a bevel periphery surface, the interior closed bore having inner screw threads; (b) said tapered shaft section of said implantable body being press-fitted within said tapered alveolus of said jawbone such that said divergent head section rests above said jawbone, said tapered shaft section having a plurality of spaced apart transverse annular grooves and a longitudinal groove extending upwardly from said narrow distal end to the middle of said tapered shaft section, where the plurality of spaced apart transverse annular grooves and the longitudinal groove provide a greater surface area into which bone growth are formed to prevent said implantable body from vertical and rotational movements within said jawbone; and (c) said narrow distal end of said tapered shaft section of said implantable body having an arch shaped gap for allowing bone growth therein to further prevent said implantable body from rotational movements.

Defined also alternatively in detail, the present invention is an anatomic dental implant fixture for lower anterior teeth and implantable in a tapered alveolus of a patient's jawbone, the implant fixture comprising: (a) an implantable body having an elongated tapered shaft section with a narrow distal end, a divergent head section with a widened proximal end, and an off-center interior closed bore extending downwardly from the widened proximal end to the middle of the tapered shaft section, the widened proximal end having a generally rounded isosceles triangle shape with a bevel periphery surface, the interior closed bore having inner screw threads; (b) a generally hexagonal shaped nut integrally connected to said rounded isosceles triangle shaped proximal end of said head section of said implantable body and having an interior bore therethrough and aligned with said off-center interior closed bore of said implantable body; (c) said tapered shaft section of said implantable body being press-fitted within said tapered alveolus of said jawbone such that said divergent head section rests above said jawbone, said tapered shaft section having a plurality of spaced apart transverse annular grooves and a longitudinal groove extending upwardly from said narrow distal end to the middle of said tapered shaft section, where the plurality of spaced apart transverse annular grooves and the longitudinal groove provide a greater surface area into which bone growth are formed to prevent said implantable body from vertical and rotational movements within said jawbone; and (d) said narrow distal end of said tapered shaft section of said implantable body having an arched shaped gap for allowing bone growth therein to further prevent said implantable body from rotational movements.

Further defined broadly, the present invention is an implant for posterior and anterior teeth and implantable in an alveolus of a patient's jawbone, the implant comprising: (a) a body having a shaft section and a head section; (b) said head section having a proximal end with at least one bevel periphery surface; and (c) said shaft section being press-fitted within said alveolus of said jawbone and having anti-movement means.

Defined further alternatively in detail, the present invention is an anatomical restoration dental implant system for posterior and anterior teeth, which is implantable in a tapered alveolus of a patient's jawbone, the implant system comprising: (a) a dental implant fixture having a tapered shaft section with a narrow distal end, a divergent head section with a widened proximal end, and an off-center stepped interior closed bore extending downwardly from the widened proximal end to the middle of the tapered shaft section, the widened proximal end having a bevel periphery surface, the interior closed bore having inner threads; (b) said tapered shaft section of said implant fixture being press-fitted within said tapered alveolus of said jawbone such that said divergent head section rests above said jawbone, said tapered shaft section having a plurality of spaced apart transverse annular grooves and a longitudinal groove extending upwardly from said narrow distal end to the middle of said tapered shaft section, where the plurality of spaced apart transverse annular grooves and the longitudinal groove provide a greater surface area into which bone growth are formed to prevent said implant fixture from vertical and rotational movements within said jawbone; (c) said narrow distal end of said tapered shaft section of said implant fixture having an arched shaped gap for allowing bone growth therein to further prevent said implant fixture from rotational movements; (d) a matching abutment member for supporting a tooth analogue and having a widened proximal portion with a proximal end, a narrow distal end with an opening, a stepped interior bore extending from the distal end to the proximal end, the widened proximal portion having a complementary interior bevel periphery surface surrounding the stepped interior bore; (e) said proximal end of said widened proximal portion of said abutment member installed over said widened proximal end of said head section of said implant fixture such that said complementary interior bevel periphery surface of said abutment member abuts against said bevel periphery surface of said widened proximal end of said implant fixture, where said widened proximal portion of said abutment member matches with said widened proximal end of said implant fixture; and (f) a bolt member having a widened head segment and a shaft segment with outer threads, the bolt member inserted into said stepped interior bore of said abutment member such that the head segment rests therein and the outer threads of the shaft segment are threadedly engaged with said inner threads of said off-center interior bore of said implant fixture, thereby securing said abutment member to said implant fixture.

Defined further alternatively broadly, the present invention is a dental implant system for posterior and anterior teeth and implantable in an alveolus of a patient's jawbone, the implant system comprising: (a) an implant having a shaft section and a head section with at least one bevel periphery surface; (b) said shaft section of said implant being press-fitted within said alveolus of said jawbone and having anti-movement means; (c) an abutment for supporting a tooth analogue and having a bottom end with at least one complementary bevel periphery surface, the abutment installed on said head section of said implant such that the at least one complementary bevel periphery surface of the abutment abuts against said at least one bevel periphery surface of said head section of said implant, where the bottom end of the abutment matches said head section of said implant; and (d) means for securing said abutment to said implant.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. An anatomic dental implant fixture for posterior teeth and implantable in a tapered alveolus of a patient's jawbone, the implant fixture comprising:

a. an implantable body having an elongated tapered shaft section with a narrow distal end, a divergent head section with a widened proximal end, and an off-center stepped interior closed bore extending downwardly from the widened proximal end to a middle of the tapered shaft section, the widened proximal end having an elliptical shape with a bevel periphery surface, the interior closed bore having inner screw threads;

b. said tapered shaft section of said implantable body for press-fitting within said tapered alveolus of said jawbone such that said divergent head section rests above said jawbone, said tapered shaft section having a plurality of spaced apart transverse annular grooves and a longitudinal groove extending upwardly from said narrow distal end to the middle of said tapered shaft section, where the plurality of spaced apart transverse annular grooves and the longitudinal groove provide a greater surface area into which bone growth are formed to prevent said implantable body from vertical and rotational movements within said jawbone; and c. said narrow distal end of said tapered shaft section of said implantable body having an arch shaped gap for allowing bone growth therein to further prevent said implantable body from rotational movements.

2. The dental implant fixture in accordance with claim 1 further comprising a small screw for temporary covering said off-center stepped interior closed bore of said implantable body to prevent growth of the gingival tissues within said off-center stepped interior closed bore.

3. The dental implant fixture in accordance with claim 1 further comprising a matching abutment member for supporting a tooth analogue and having a widened proximal portion with a proximal protruding truncated cone shaped engagement end, a narrow distal end with an opening, and a stepped interior bore extending from the distal end to the proximal protruding truncated cone shaped engagement end, the widened proximal portion having a generally elliptical shape with a complementary interior bevel periphery surface.

4. The dental implant fixture in accordance with claim 3 wherein said protruding engagement end of said abutment member inserts into said off-center interior bore of said implantable body such that said complementary interior bevel periphery surface abuts against said bevel periphery surface of said widened proximal end of said implantable body, where said widened elliptical proximal portion of said abutment member matches with said widened elliptical proximal end of said implantable body.

5. The dental implant fixture in accordance with claim 1 further comprising a bolt member having a widened head segment and an elongated shaft segment with outer screw threads, the head segment having a top notch for adapting a driving tool.

6. The dental implant fixture in accordance with claim 5 wherein said bolt member inserts into said stepped interior bore of said abutment member at said opening of said narrow distal end of said abutment member, where said head segment rests therein and said outer screw threads of said shaft segment of said bolt member are threadedly engaged with said inner screw threads of said off-center interior closed bore of said implantable body, thereby securing said abutment member to said implantable body.

7. The dental implant fixture in accordance with claim 1 wherein said widened proximal end of said implantable body further comprises means adaptable with a dental tool for orienting said implantable body.

8. The dental implant fixture in accordance with claim 7 wherein said means adaptable with a dental tool for orienting said implantable body includes two small opposite closed apertures.

9. An anatomic dental implant fixture for upper anterior teeth and implantable in a tapered alveolus of a patient's jawbone, the implant fixture comprising:

a. an implantable body having an elongated tapered shaft section with a narrow distal end, a divergent head section with a widened proximal end, and an off-center stepped interior closed bore extending downwardly from the widened proximal end to a middle of the tapered shaft section, the widened proximal end having a generally rounded equilateral triangle shape with a bevel periphery surface, the interior closed bore having inner screw threads;

b. said tapered shaft section of said implantable body for press-fitting within said tapered alveolus of said jawbone such that said divergent head section rests above said jawbone, said tapered shaft section having a plurality of spaced apart transverse annular grooves and a longitudinal groove extending upwardly from said narrow distal end to the middle of said tapered shaft section, where the plurality of spaced apart transverse annular grooves and the longitudinal groove provide a greater surface area into which bone growth are formed to prevent said implantable body from vertical and rotational movements within said jawbone; and c. said narrow distal end of said tapered shaft section of said implantable body having an arch shaped gap for allowing bone growth therein to further prevent said implantable body from rotational movements.

10. The dental implant fixture in accordance with claim 9 further comprising a small screw for temporary covering said off-center stepped interior closed bore of said implantable body to prevent growth of the gingival tissues within said off-center stepped interior closed bore.

11. The dental implant fixture in accordance with claim 9 further comprising a matching abutment member for supporting a tooth analogue and having a widened proximal portion with a proximal protruding truncated cone shaped engagement end, a narrow distal end with an opening, and a stepped interior bore extending from the distal end to the proximal protruding truncated cone shaped engagement end, the widened proximal portion having a generally rounded equilateral triangle shape with a complementary interior bevel periphery surface.

12. The dental implant fixture in accordance with claim 11 wherein said protruding engagement end of said abutment member inserts into said off-center interior closed bore of said implantable body such that said complementary interior bevel periphery surface abuts against said bevel periphery surface of said widened proximal end of said implantable body, where said rounded equilateral triangle shaped proximal portion of said abutment member matches with said rounded equilateral triangle shaped proximal end of said implantable body.

13. The dental implant fixture in accordance with claim 9 further comprising a bolt member having a widened head segment and an elongated shaft segment with outer screw threads.

14. The dental implant fixture in accordance with claim 13 wherein said bolt member inserts into said stepped interior bore of said abutment member at said opening of said narrow distal end of said abutment member, where said head segment rests therein and said outer screw threads of said shaft segment of said bolt member are threadedly engaged with said inner screw threads of said off-center interior bore of said implantable body, thereby securing said abutment member to said implantable body.

15. The dental implant fixture in accordance with claim 9 wherein said rounded equilateral triangle proximal end of said implantable body further comprises means adaptable with a dental tool for orienting said implantable body.

16. The dental implant fixture in accordance with claim 15 wherein said means adaptable with a dental tool for orienting said implantable body includes two small opposite closed apertures.

17. An anatomic dental implant fixture for lower anterior teeth and implantable in a tapered alveolus of a patient's jawbone, the implant fixture comprising:

a. an implantable body having an elongated tapered shaft section with a narrow distal end, a divergent head section with a widened proximal end, and an off-center interior closed bore extending downwardly from the widened proximal end to a middle of the tapered shaft section, the widened proximal end having a generally rounded isosceles triangle shape with a bevel periphery surface, the interior closed bore having inner screw threads;

b. a generally hexagonal shaped nut integrally connected to said rounded isosceles triangle shaped proximal end of said head section of said implantable body and having an interior bore therethrough and aligned with said off-center interior closed bore of said implantable body;

c. said tapered shaft section of said implantable body for press-fitting within said tapered alveolus of said jawbone such that said divergent head section rests above said jawbone, said tapered shaft section having a plurality of spaced apart transverse annular grooves and a longitudinal groove extending upwardly from said narrow distal end to the middle of said tapered shaft section, where the plurality of spaced apart transverse annular grooves and the longitudinal groove provide a greater surface area into which bone growth are formed to prevent said implantable body from vertical and rotational movements within said jawbone; and d. said narrow distal end of said tapered shaft section of said implantable body having an arched shaped gap for allowing bone growth therein to further prevent said implantable body from rotational movements.

18. The dental implant fixture in accordance with claim 17 further comprising a cover cap for temporary covering said hexagonal shaped nut and said rounded isosceles shaped proximal end of said divergent head section of said implantable body to prevent growth of the gingival tissues with said off-center interior closed bore.

19. The dental implant fixture in accordance with claim 17 further comprising a matching abutment member for supporting a tooth analogue and having a generally truncated cone shaped body, the truncated cone shaped body having a generally rounded isosceles triangle shaped proximal portion with a matching proximal hexagonal recess, a narrow distal end with a circular opening, and a stepped interior bore extending from the distal end to the proximal recess, the rounded isosceles triangle shaped proximal portion further having a complementary interior bevel periphery surface.

20. The dental implant fixture in accordance with claim 19 wherein said matching proximal hexagonal recess of said abutment member covers over said hexagonal shaped nut such that said complementary interior bevel periphery surface abuts against said bevel periphery surface of said rounded isosceles triangle proximal end of said head section of said implantable body, where said rounded isosceles triangle shaped proximal portion of said abutment member matches with said rounded isosceles triangle shaped proximal end of said implantable body.

21. The dental implant fixture in accordance with claim 17 further comprising a bolt member having a widened head segment and an elongated shaft segment with outer screw threads, the head segment having a top notch for adapting a driving tool.

22. The dental implant fixture in accordance with claim 21 wherein said bolt member inserts into said stepped interior bore of said abutment member at said opening of said narrow distal end of said abutment member, where said head segment rests therein and said outer screw threads of said shaft segment of said bolt member are threadedly engaged with said inner screw threads of said off-center interior closed bore of said implantable body, thereby securing said abutment member to said implantable body.

23. An implant for posterior and anterior teeth and implantable in an alveolus of a patient's jawbone, the implant comprising:

a. a body having a shaft section, a head section and an off-center interior bore extending from the head section to the shaft section;

b. said head section having a proximal end with at least one bevel periphery surface; and c. said shaft section for press-fitting within said alveolus of said jawbone and having anti-movement means.

24. The implant in accordance with claim 23 wherein said anti-movement means include at least one transverse annular groove.

25. The implant in accordance with claim 23 wherein said anti-movement means include at least one vertical groove.

26. The implant in accordance with claim 23 wherein said anti-movement means include an arch shaped gap located at a distal end of said tapered shaft.

27. The implant in accordance with claim 23 further comprising a matching abutment member for supporting a tooth analogue, the abutment member having a proximal end with at least one complementary bevel periphery surface, such that when the abutment member installs on said body, said complementary bevel periphery surface of the abutment member abuts against said at least one bevel periphery surface of said proximal end of said head section of said body.

28. The implant in accordance with claim 27 further comprising means for securing said abutment member to said body.

29. The implant in accordance with claim 27 wherein said proximal end of said abutment member is generally an elliptical shape.

30. The implant in accordance with claim 27 wherein said proximal end of said abutment member is generally a rounded equilateral triangle shape.

31. The implant in accordance with claim 27 wherein said proximal end of said abutment member is generally a rounded isosceles triangle shape.

32. The implant in accordance with claim 23 wherein said proximal end of said head section of said body is generally an elliptical shape.

33. The implant in accordance with claim 23 wherein said proximal end of said head section of said body is generally a rounded equilateral triangle shape.

34. The implant in accordance with claim 23 wherein said proximal end of said head section of said body is generally a rounded isosceles triangle shape.

35. An anatomical restoration dental implant system for posterior and anterior teeth, which is implantable in a tapered alveolus of a patient's jawbone, the implant system comprising:

a. a dental implant fixture having a tapered shaft section with a narrow distal end, a divergent head section with a widened proximal end, and an off-center stepped interior closed bore extending downwardly from the widened proximal end to a middle of the tapered shaft section, the widened proximal end having a bevel periphery surface, the interior closed bore having inner threads;

b. said tapered shaft section of said implant fixture for press-fitting within said tapered alveolus of said jawbone such that said divergent head section rests above said jawbone, said tapered shaft section having a plurality of spaced apart transverse annular grooves and a longitudinal groove extending upwardly from said narrow distal end to the middle of said tapered shaft section, where the plurality of spaced apart transverse annular grooves and the longitudinal groove provide a greater surface area into which bone growth are formed to prevent said implant fixture from vertical and rotational movements within said jawbone;

c. said narrow distal end of said tapered shaft section of said implant fixture having an arched shaped gap for allowing bone growth therein to further prevent said implant fixture from rotational movements;

d. a matching abutment member for supporting a tooth analogue and having a widened proximal portion with a proximal end, a narrow distal end with an opening, and a stepped interior bore extending from the distal end to the proximal end, the widened proximal portion having a complementary interior bevel periphery surface surrounding the stepped interior bore;

e. said proximal end of said widened proximal portion of said abutment member installed over said widened proximal end of said head section of said implant fixture such that said complementary interior bevel periphery surface of said abutment member abuts against said bevel periphery surface of said widened proximal end of said implant fixture, where said widened proximal portion of said abutment member matches with said widened proximal end of said implant fixture; and f. a bolt member having a widened head segment and a shaft segment with outer threads, the bolt member inserted into said stepped interior bore of said abutment member such that the head segment rests therein and the outer threads of the shaft segment are threadedly engaged with said inner threads of said off-center interior bore of said implant fixture, thereby securing said abutment member to said implant fixture.

36. The implant system in accordance with claim 35 further comprising a small screw for temporary covering said off-center stepped interior closed bore to prevent gingival tissues from growing therein.

37. The implant system in accordance with claim 35 wherein said stepped interior bore of said abutment member further comprises inner threads, where said outer threads of said shaft segment of said bolt member are threadedly engaged with the inner threads of said abutment member, thereby interlocking said bolt member to said abutment member.

38. The implant system in accordance with claim 35 wherein said widened proximal end of said divergent head section of said implant fixture is generally elliptical shape.

39. The implant system in accordance with claim 35 wherein said widened proximal end of said divergent head section of said implant fixture is generally a rounded triangle shape.

40. The implant system in accordance with claim 35 wherein said widened proximal portion of said abutment member is generally an elliptical shape.

41. The implant system in accordance with claim 35 wherein said widened proximal portion of said abutment member is generally a rounded triangle shape.

42. The implant system in accordance with claim 35 wherein said widened proximal end of said implant fixture further comprises means adaptable with a dental tool for orienting said implant fixture.

43. The implant system in accordance with claim 42 wherein said means adaptable with a dental tool for orienting said implant fixture includes two small opposite closed apertures.

44. The implant system in accordance with claim 35 wherein said implant fixture further comprises a hexagonal nut integrally connected to said divergent head section and having an opening therethrough a generally hexagonal nut integrally connected to said widened proximal end of said head section of said implant fixture and having an interior bore therethrough and aligned with said off-center stepped interior closed bore of said implant fixture.

45. The implant system in accordance with claim 44 wherein said abutment member further has a hexagonal shaped recess which matches said hexagonal nut on said head section of said implant fixture.

46. A dental implant system for posterior and anterior teeth and implantable in an alveolus of a patient's jawbone, the implant system comprising:
   a. an implant having a shaft section, a head section with at least one bevel periphery surface, and an off-center interior bore extending from the head section to the shaft section;
   b. said shaft section of said implant for press-fitting within said alveolus of said jawbone and having anti-movement means;
   c. an abutment for supporting a tooth analogue and having a bottom end with at least one complementary bevel periphery surface, the abutment installed on said head section of said implant such that the at least one complementary bevel periphery surface of the abutment abuts against said at least one bevel periphery surface of said head section of said implant, where the bottom end of the abutment matches said head section of said implant; and
   d. means for securing said abutment to said implant.

47. The implant system in accordance with claim 46 wherein said head section of said implant further comprises means adaptable with a dental tool for orienting said implant.

48. The implant system in accordance with claim 47 wherein said means adaptable with a dental tool for orienting said implant includes two opposite closed apertures.

49. The implant system in accordance with claim 46 wherein said head section of said implant is generally elliptical shape.

50. The implant system in accordance with claim 46 wherein said head section of said implant is generally a rounded triangle shape.

51. The implant system in accordance with claim 46 wherein said bottom end of said abutment is generally an elliptical shape.

52. The implant system in accordance with claim 46 wherein said bottom end of said abutment is generally a rounded triangle shape.

53. The implant system in accordance with claim 46 wherein said implant further comprises a nut integrally connected to said head section.

54. The implant system in accordance with claim 53 wherein said abutment further has a matching recess which is located on said bottom end and matches said nut on said head section of said implant.

55. The implant system in accordance with claim 46 wherein said anti-movement means include at least one transverse annular groove.

56. The implant system in accordance with claim 46 wherein said anti-movement means include at least one vertical groove for providing a surface area into which bone growth is formed to prevent said implant from rotational movements.

57. The implant system in accordance with claim 46 wherein said anti-movement means include an arch shaped gap located on a bottom end of said shaft section of said implant for allowing bone growth therein to further prevent said implant from rotational movements.

58. An anatomic dental implant fixture for posterior teeth and implantable in a tapered alveolus of a patient's jawbone, the implant fixture comprising: an implantable body having an elongated tapered shaft section with a narrow distal end, a divergent head section with a widened proximal end, and an off-center stepped interior closed bore extending downwardly from the widened proximal end to a middle of the tapered shaft section, the widened proximal end having an elliptical shape with a bevel periphery surface, the interior closed bore having inner screw threads.

59. An anatomic dental implant fixture for upper anterior teeth and implantable in a tapered alveolus of a patient's jawbone, the implant fixture comprising: an implantable body having an elongated tapered shaft section with a narrow distal end, a divergent head section with a widened proximal end, and an off-center stepped interior closed bore extending downwardly from the widened proximal end to a middle of the tapered shaft section, the widened proximal end having a generally rounded equilateral triangle shape with a bevel periphery surface, the interior closed bore having inner screw threads.

60. An anatomic dental implant fixture for lower anterior teeth and implantable in a tapered alveolus of a patient's jawbone, the implant fixture comprising: an implantable body having an elongated tapered shaft section with a narrow distal end, a divergent head section with a widened proximal end, and an off-center interior closed bore extending downwardly from the widened proximal end to the middle of the tapered shaft section, the widened proximal end having a generally rounded isosceles triangle shape with a bevel periphery surface, the interior closed bore having inner screw threads.

61. An anatomical restoration dental implant system for posterior and anterior teeth, which is implantable in a tapered alveolus of a patient's jawbone, the implant system comprising:

a. a dental implant fixture having a tapered shaft section with a narrow distal end, a divergent head section with a widened proximal end, and an off-center stepped interior closed bore extending downwardly from the widened proximal end to a middle of the tapered shaft section, the widened proximal end having a bevel periphery surface, the interior closed bore having inner threads;

b. a matching abutment member for supporting a tooth analogue and having a widened proximal portion with a proximal end, a narrow distal end with an opening, and a stepped interior bore extending from the distal end to the proximal end, the widened proximal portion having a complementary interior bevel periphery surface surrounding the stepped interior bore;

c. said proximal end of said abutment member installed over said widened proximal end of said head section of said implant fixture such that said complementary interior bevel periphery surface of said abutment member abuts against said bevel periphery surface of said widened proximal end of said implant fixture, where said widened proximal portion of said abutment member matches with said widened proximal end of said implant fixture; and d. means for securing said abutment member to said implant fixture.

* * * * *